Figure 1:
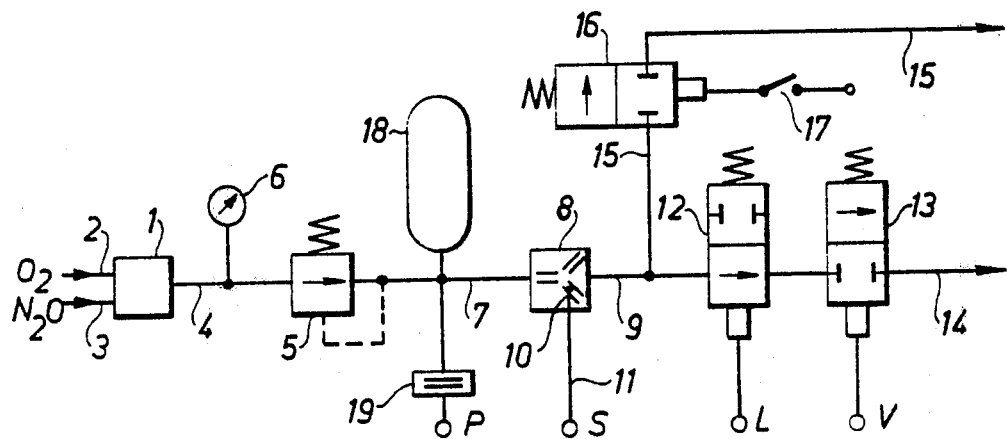

United States Patent [19]

Berndtsson

[11] 4,241,732

[45] Dec. 30, 1980

[54] ARRANGEMENT IN RESPIRATORS USING A FLUIDISTOR TO DETERMINE VOLUME OF AIR PASSED TO A PATIENT AND PRESSURE SENSOR TO CORRECT VOLUME READING IN TERMS OF ACTUAL PRESSURE

[75] Inventor: Christer Berndtsson, Lidingö, Sweden

[73] Assignee: AGA Aktiebolag, Lidingo, Sweden

[21] Appl. No.: 961,206

[22] Filed: Nov. 16, 1978

[30] Foreign Application Priority Data

Nov. 29, 1977 [SE] Sweden .............................. 7713464

[51] Int. Cl.$^3$ .................................................. A61M 16/00
[52] U.S. Cl. ........................... 128/204.24; 128/204.21
[58] Field of Search ............... 128/145.5, 145.6, 145.8, 128/204.24, 716

[56] References Cited

U.S. PATENT DOCUMENTS

| | | | |
|---|---|---|---|
| 3,741,208 | 6/1973 | Jonsson et al. | 128/145.6 |
| 3,768,468 | 10/1973 | Cox | 128/145.8 |
| 3,848,591 | 11/1974 | Smythe et al. | 128/145.8 |
| 4,011,866 | 3/1977 | Klein et al. | 128/145.8 |
| 4,057,059 | 11/1977 | Reid, Jr. et al. | 128/145.8 |
| 4,127,123 | 11/1978 | Bird | 128/145.8 |

*Primary Examiner*—Kyle L. Howell
*Assistant Examiner*—Jeffrey W. Tayon

*Attorney, Agent, or Firm*—Larson, Taylor and Hinds

[57] ABSTRACT

An arrangement is provided in a respirator for measuring the amount of gas passed to a patient through a supply line. The arrangement includes a self-oscillating fluidistor for dividing the gas flow into part volumes of a given magnitude and for generating an electrical pulse for each part volume passing therethrough. The fluidistor includes two outputs and a control channel having a temperature-dependent resistor located therein and an amplifier and pulse-forming circuit connected to the resistor so as to generate electrical pulses whose number is related to the number of part volumes flowing through the control channel of the fluidistor. A binary counter is connected to the amplifier and pulse-forming circuit for counting the number of pulses over a predetermined time interval while a digital-to-analog (D/A) converter, having first and second inputs, generates an analog signal corresponding to the number of pulses produced per time interval. A pressure sensing device connected in the supply line to the patient and to one input of the D/A coverter in series with a calibrating resistance such that an electrical control voltage is produced by the pressure sensing device in response to the pressure in the supply line and is supplied to the corresponding input of the D/A converter so as to correct the output signal of the D/A converter in accordance with part volumes of a given predetermined pressure, e.g., atmospheric pressure.

4 Claims, 3 Drawing Figures

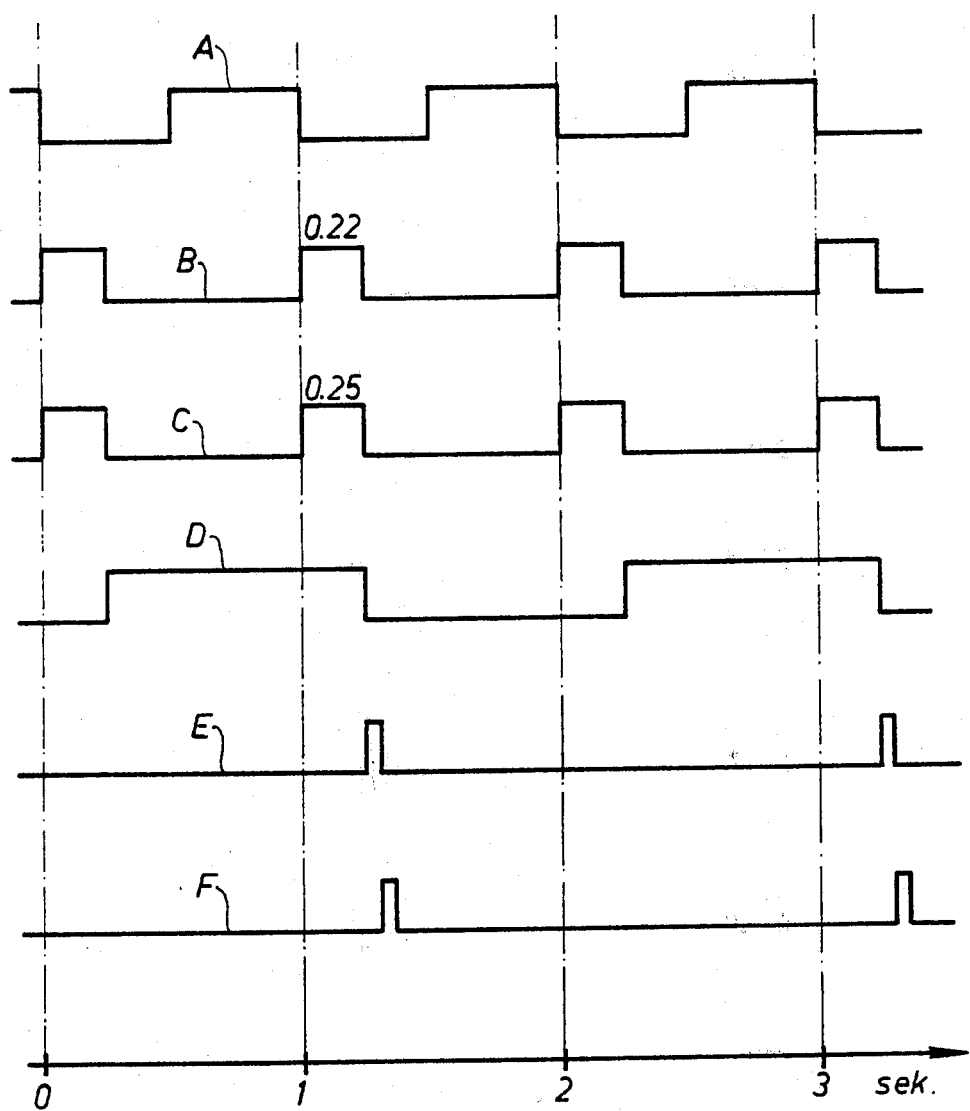

ARRANGEMENT IN RESPIRATORS USING A FLUIDISTOR TO DETERMINE VOLUME OF AIR PASSED TO A PATIENT AND PRESSURE SENSOR TO CORRECT VOLUME READING IN TERMS OF ACTUAL PRESSURE

The present invention relates to an arrangement for supplying breathing-gas passed to a patient through a respirator of the type in which there is incorporated in a supply line to the patient a means which, when the patient inhales, divides the flow of gas into part-volumes of a given magnitude, said means being arranged to generate an electric signal or pulse for each part-volume which passes through said means, and in which arrangement the electric signals are arranged to be sent to a binary counter for counting the number of signals obtained over a given interval of time.

By means of such a respirator, it is possible to adjust the amount of gas supplied to the patient per unit of time to a desired value, by controlling the pressure on the gas caused to pass through said means in said supply line.

In order to be able to establish whether the ventilation is satisfactory for a patient connected to a respirator, it is necessary to know what amount of gas per unit of time in respect of a gas under a given normal pressure, for example atmospheric pressure, corresponds to the amount of gas passed to the patient per unit of time.

When, as before mentioned, the ventilation is adjusted by changing the pressure on the gas it is possible to calculate the equivalent amount of gas per unit of time at a given normal pressure by means of tables or curve diagrams. The certainty that the amount of gas given to the patient is the correct amount increases considerably, however, when there can be obtained a direct indication of the equivalent amount of gas per unit of time.

Figure 2:
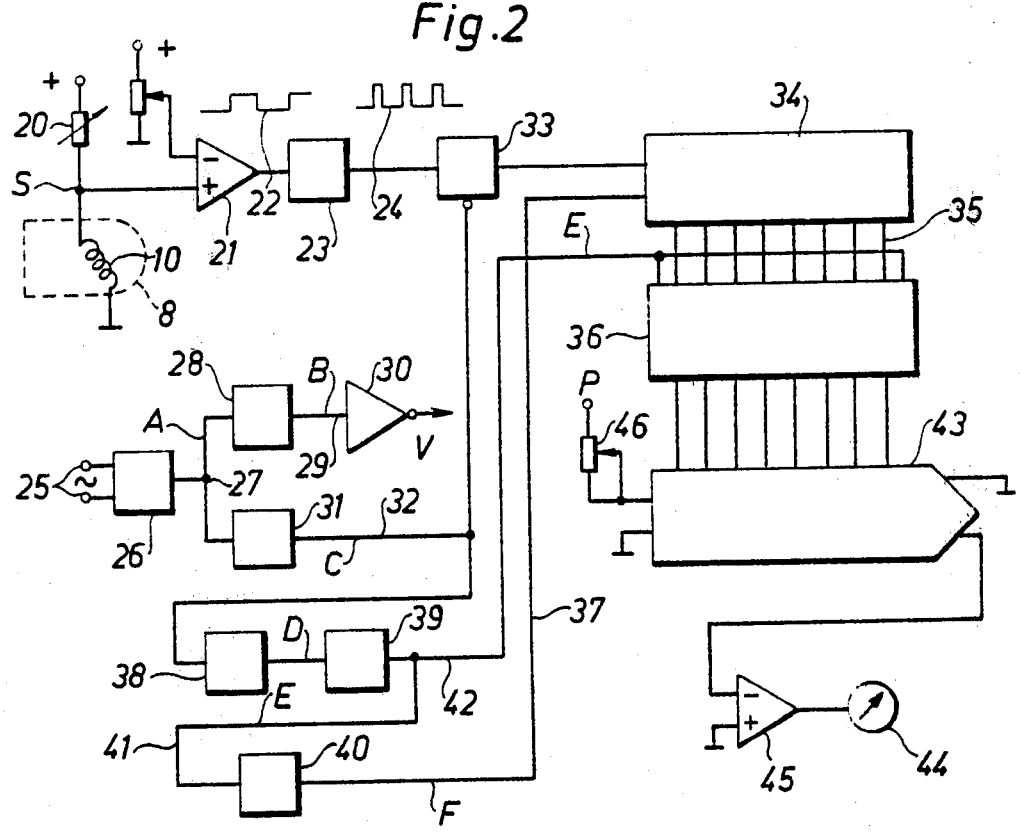

This result can be obtained by means of the present invention, which has the characterising features disclosed in the accompanying claims. An exemplary embodiment of the invention will now be described with reference to the accompanying drawing, in which FIG. 1 is a block schematic of the gas system in the respirator, and FIG. 2 is a block schematic of the electrical elements incorporated in said respirator. FIG. 3 illustrates curves of certain electrical-pulse series produced in the arrangement.

The gas system illustrated in FIG. 1 includes a gas-mixer 1 to which gases can be supplied through lines 2 and 3, said gases being, for example, oxygen or nitrous oxide. The gas-mixer 1 is connected to a pressure-regulator 5 through a line 4. Connected to the line 4 is a manometer 6. The gas is passed from the pressure-regulator 5 to a fluidistor 8 (fluidic-switching device) through a line 7. The fluidistor is designed in a known manner to be self-oscillating, in a manner such that gas passed to an inlet of the fluidistor is alternately switched between two outlets. These outlets extend to a common outlet line 9.

The gas passed to the fluidistor is divided therein into part volumes of mutually equal magnitude, said part volumes being passed to the outlet line 9. In a selected embodiment, the part-volumes may be equal to 20 ml. To enable the number of part-volumes passing through the fluidistor 8 to be counted, there is incorporated in one of its outlet passages a temperature-dependent resistance, such as a platina thread 10 heated by an electric current. The voltage across this resistance is taken out over a line 11 and is applied to a terminal or connection S.

The gas leaving the fluidistor 8 through the line 9 passes through two series-connected valves 12 and 13, whereafter the gas is supplied through a line 14 to a device, such as a tracheal tube, connected to the patient.

The valves 12 and 13 are actuated partly by the force of the springs shown in the drawing, and partly by electro-magnets, the valve 12, which acts as a warning and safety valve, being open when its electro-magnet is energised by the fact that a voltage is applied to a terminal or connection L. In a manner hereinafter described, a control voltage is passed to the electro-magnet for the valve 13 over a terminal or connection V in a manner such that the valve 13 is opened over a given interval of time to permit breathing gas to be blown or injected into the patient, and to be closed over intermediate intervals of time to enable the patient to breath out.

Before anaesthetizing a patient to an extent such that a tracheal tube can be inserted, it might be desirable to ventilate the patient with the aid of a breathing mask. To this end there is connected to the line 9 a line 15 which has incorporated therein a valve 16 controlled by an electro-magnet. Arranged in a control line to the electro-magnet of the valve is a switch 17 which when closed opens the valve 16 so that gas is passed continuously to a breathing mask connected to said line.

When the valve 13 is open for feeding breathing gas to the patient, the amounts of gas flowing through the lines 7, 9 and 14 may be of such high magnitude that they cannot be delivered from the gas mixer 1 and the pressure regulator 5. For this reason there is connected to the line 7 a container of larger volume in the form of a vessel 18 which, in the described embodiment, can hold a volume of 5 liters. Breathing gas is continuously charged to said vessel through the pressure regulator 5 during the aforementioned intermediate time intervals, said vessel supplying gas through the lines 7, 9 and 14 during those time intervals when air is injected into the patient. This injection of air into the patient takes place over an interval of time which is much shorter than the aforementioned intermediate time intervals.

As previously mentioned, the flow of gas through the lines 7 and 9 is divided into part volumes of mutually equal magnitude by means of the fluidistor 8. Thus, the number of part volumes obtained over a given time interval can be determined, to assess the amount of gas passed to the patient. In view of the fact, however, that the pressure on the gas can be adjusted, to enable the desired ventilation of a patient, it must be possible to reduce the thus determined amount of gas to an equivalent amount of gas of a given pressure, for example atmospheric pressure. To this end, there is connected to the line 7 a pressure transducer 19 of such construction that there occurs at a connection P associated with the pressure transducer an electric voltage which is proportional to the gas pressure in the line 7. The pressure transducer 19 may contain, in a known manner, a piezo-resistive resistor.

As will be seen from FIG. 2, the temperature-dependent resistance 10 incorporated in the fluidistor 8, shown in dash lines, is connected between the point S and earth. The resistor 10 is heated by a current supplied from a positive connection through a control resistor 20. When the flow of gas from the line 7 to the line 9 passes through the fluidistor 8, the said gas flow will pulsate in the outlet of the fluidistor in which the temperature-dependent resistor 10 is arranged.

As a result hereof the resistance of the resistor 10 will change periodically and a varying voltage will be obtained at the connection S. This is passed to an amplifying chain, which is represented symbolically in FIG. 2 by an operational amplifier 21. As a result hereof a square wave as illustrated in FIG. 2 will be formed in the output line 22. This square wave is passed to a pulse-forming network 23 in a manner such that a series of pulses occur in the output line of said network, each pulse corresponding to a change in the square wave. The number of pulses occurring in the output line 24 over a given time interval is a measurement of the amount of gas passing through the fluidistor 8 over the same time interval.

The frequency at which air is injected and the relationship between the air-injection time and the exhalation time over a period of time can be arbitrarily selected. Thus, operating current can be supplied to the electro-magnets in the valve 13 at a frequency such that there is obtained approximately 20 air-injection operations per minute. In the illustrated embodiment, however, it is assumed that 60 air-injection operations per minute are obtained by means of the valve 13, and that the relationship between the air-injection time and the exhalation time is selected so that air is injected into the patient over a time of 0.22 seconds and exhalation takes place over an intermediate time interval of 0.78 seconds.

The control signal to the valve 13 is obtained from the net frequency 50 Hz, which is applied to terminals 25 and is rectified and the frequency divided in a net system 26 of known design, such that there is obtained in the output line 27 from the net 26 a pulse frequency of 1 Hz, as illustrated by the curve A in FIG. 3. This pulse frequency is applied to a monostable stage or flip-flop 28 which is so dimensioned that there is obtained on its output 29 a square wave as shown in the curve B in FIG. 3. This wave has a certain amplitude for a period of 0.22 seconds and another amplitude for a period of 0.78 seconds. It is applied over an inverter 30 to the terminal V and from there to the valve 13, said valve being periodically open for 0.22 seconds and closed for 0.78 seconds.

The pulse frequency of 1 Hz occurring in the line 27 is also applied to a further monostable stage or flip-flop 31 which is dimensioned in a manner such that there occurs at its output 32 a square wave as shown in curve C in FIG. 3, said wave exhibiting mutually different amplitudes for 0.25 seconds and 0.75 seconds. This square wave is arranged to control a gate circuit 33 connected between the pulse-forming network 23 and a binary counter 34. The two monostable flip-flops 28 and 31 are mutually synchronised in a manner such that the gate circuit 33 is open to permit the pulses in the line 24 to pass to the counter 34 over a period of 0.25 seconds at the same time as the valve 13 is open to permit gas to be injected into the patient.

The binary counter 34 converts the incoming pulses to an 8-bit parallel binary word which is transmitted, over a plurality of connecting lines 35, to a register 36 comprising 8 stages or flip-flops. This 8-bit binary word is transmitted every other second under the influence of a control pulse passed through a line 37. This control pulse is generated by means of a bistable stage or flip-flop 38 and two monostable stages or flip-flops 39 and 40 mutually connected in series, said monostable flip-flops being connected to the output line 32 from the monostable flip-flop 31 and together causing the frequency to be halved. The output signal from the bistable flip-flop 38 is represented in FIG. 3 by the curve D and the output signal from the monostable flip-flop 39 by the curve E. Thus, there occurs every other second in the line 37 a pulse shown as the curve F in FIG. 3, this pulse being passed to the binary counter 34 to set said counter to zero, thereby to enable a new measuring cycle to commence. Extending from the connecting line 41 to the register 36, between the monostable flip-flop 39 and 40, is a control line 42 in which the series of pulses shown by curve E occurs at a frequency of 0.5 Hz, which controls the read-in in the register 36.

The control signals from the register 36 are sent to a digital-analogue converter 43, to the output of which there is connected an indicating instrument 44 over an amplifying chain, which is illustrated schematically in FIG. 2 by an operation amplifier 45.

The indication given by the instrument 44 will be proportional to the number of pulses which are stored in the register 36 over each measuring period. Thus, a larger number of pulses stored in the register corresponds to a greater indication on the indicating instrument. Consequently, because each pulse corresponds to an amount of gas passing through the fluidistor 8, as previously mentioned, the instrument 44 can be graduated in, for example, liters per minute.

As before mentioned, it is desirable to be able to determine the amount of gas at a given pressure, for example atmospheric pressure, which corresponds to the amount of gas passed to the patient. To this end, the aforementioned pressure transducer 19 is connected to the gas line 7, in a manner such that occurs at the connection P a voltage which is proportional to the gas pressure in the line 7. This voltage is applied to the terminal P in FIG. 2 in a manner such that it can be passed to a control input of a digital analogue converter 43 over a calibrating resistance 46. As a result hereof, the output current from the digital-analogue converter 43 will correspond to the product of the voltage at the terminal P and the signal supplied from the register 36. The indicating instrument 44 can thus be graduated to give the equivalent amount of gas at a given pressure, for example atmospheric pressure.

I claim:

1. An arrangement for use in a respirator for measuring the amount of gas passed to a patient through a supply line, said arrangement comprising means disposed in the supply line to the patient for dividing the gas flow into part volumes of a given magnitude and for generating an electrical pulse for each part volume passing therethrough, said means comprising a self-oscillating fluidistor having two outputs and including a control channel having a temperature-dependent resistance located therein and an amplifier and pulse-forming means connected to said resistance for generating electrical pulses whose number is related to the part volumes flowing through said control channel, said arrangement further comprising a binary counter connected to said amplifier and pulse-forming means for counting the number of electrical pulses produced by said amplifier and pulse-forming means over a predetermined time interval, a digital-to-analog converter, having first and second inputs, for generating an analog signal corresponding to the number of pulses produced per said time interval by said amplifier and pulse-forming means, said first input of said digitial-to-analog converter being connected to the output of said amplifier and pulse-forming means, and a pressure-sensing means connected in said supply line to the patient and to said second input of said digital-to-analog converter in series with a calibrating resistance for producing an electrical control voltage in response to the pressure in said supply line and for applying said electrical control voltage to said second input of said digital-to-analog converter so as to correct the output signal of said conveter in accordance with part volumes of a given predetermined pressure.

2. An arrangement as claimed in claim 1, wherein the voltage across said temperature dependent resistance is substantially rectangular in wave-form, and said amplifier and pulse-forming means generate a pulse in response to each change in the voltage wave-form across said temperature-dependent resistance so that each said pulse generated by said amplifier and pulse-forming means corresponds to a part volume of the gas passing through the fluidistor.

3. An arrangement as claimed in claim 1, wherein said temperature-dependent resistance comprises a platina wire heated by electric current.

4. An arrangement as claimed in claim 1, wherein said pressure-sensing means comprises a piezo-resistive resistor.

* * * * *